(12) United States Patent
Luebke et al.

(10) Patent No.: US 9,957,449 B2
(45) Date of Patent: May 1, 2018

(54) PROCESS FOR THE PRODUCTION OF JET-RANGE HYDROCARBONS BY OLIGOMERIZATION OF RENEWABLE OLEFINS HAVING 3 TO 8 CARBONS

(71) Applicant: UOP LLC, Des Plaines, IL (US)

(72) Inventors: Charles P. Luebke, Mount Prospect, IL (US); Geoffrey W. Fichtl, Chicago, IL (US); Dana K. Sullivan, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days. days.

(21) Appl. No.: 14/695,352

(22) Filed: Apr. 24, 2015

(65) Prior Publication Data

US 2016/0312131 A1 Oct. 27, 2016

(51) Int. Cl.
*C10G 69/00* (2006.01)
*C10G 50/00* (2006.01)
*C10L 1/04* (2006.01)
*C07C 2/08* (2006.01)
*C07C 2/04* (2006.01)
*C07C 2/12* (2006.01)
*C07C 2/02* (2006.01)
(Continued)

(52) U.S. Cl.
CPC .............. *C10G 50/00* (2013.01); *C07C 2/02* (2013.01); *C07C 2/04* (2013.01); *C07C 2/06* (2013.01); *C07C 2/08* (2013.01); *C07C 2/12* (2013.01); *C10G 69/126* (2013.01); *C10G 2300/1088* (2013.01); *C10G 2400/08* (2013.01); *C10L 2200/043* (2013.01); *C10L 2200/0469* (2013.01); *C10L 2270/04* (2013.01)

(58) Field of Classification Search
CPC ...... C10G 69/126; C10G 57/02; C10G 50/00; C10L 1/04; C10L 2290/24; C10L 2270/04; C10L 2200/043; C10L 2290/543; C10L 2290/10
See application file for complete search history.

(56) References Cited

U.S. PATENT DOCUMENTS

| | | | |
|---|---|---|---|
| 5,347,064 A | 9/1994 | Child et al. | |
| 7,161,054 B2 * | 1/2007 | Heidemann | C07C 2/10 585/503 |
| 8,183,425 B2 | 5/2012 | Luo et al. | |

(Continued)

OTHER PUBLICATIONS

Lew et al., "Meet the greater demand for high-octane blending agents with HF alkylation," Fuel Reformulation (1994), 4(2), 58-62.

(Continued)

*Primary Examiner* — In Suk C Bullock
*Assistant Examiner* — Ali Z Fadhel

(57) ABSTRACT

Processes for producing jet-range hydrocarbons includes splitting a renewable olefin feedstock comprising $C_3$ to $C_8$ olefins into a plurality of streams and passing each stream to an oligomerization reactor containing a zeolite catalyst to produce an oligomerized effluent. The reactors may be arranged in series, such that an oligomerized effluent comprises a diluent for a downstream reactor. The net oligomerized effluent may be separated and a heavy olefin stream comprising $C_{8+}$ olefins may be hydrogenated and separated to provide a distillate range hydrocarbon product.

11 Claims, 1 Drawing Sheet

(51) Int. Cl.
*C07C 2/06* (2006.01)
*C10G 69/12* (2006.01)

(56) References Cited

U.S. PATENT DOCUMENTS

| | | | |
|---|---|---|---|
| 2005/0182284 A1* | 8/2005 | Stanat | C07C 2/12 585/535 |
| 2007/0049781 A1* | 3/2007 | Brown | C10G 50/00 585/517 |
| 2007/0173676 A1* | 7/2007 | Brown | C07C 2/18 585/533 |
| 2007/0191661 A1* | 8/2007 | Brown | C07C 2/12 585/517 |
| 2012/0197053 A1* | 8/2012 | Cantrell | B01J 21/04 585/251 |
| 2014/0051897 A1* | 2/2014 | Peters | C10G 3/42 585/13 |
| 2014/0134059 A1 | 5/2014 | Nicholas et al. | |
| 2014/0249340 A1* | 9/2014 | Tom | C07C 1/24 585/255 |
| 2015/0158786 A1* | 6/2015 | Mertens | B01J 20/08 585/518 |

OTHER PUBLICATIONS

Rhodes, Anne K., "New process schemes, retrofits, fine tune alkylation capabilities," Oil and Gas Journal (1994), 92(34), 56-59.

* cited by examiner

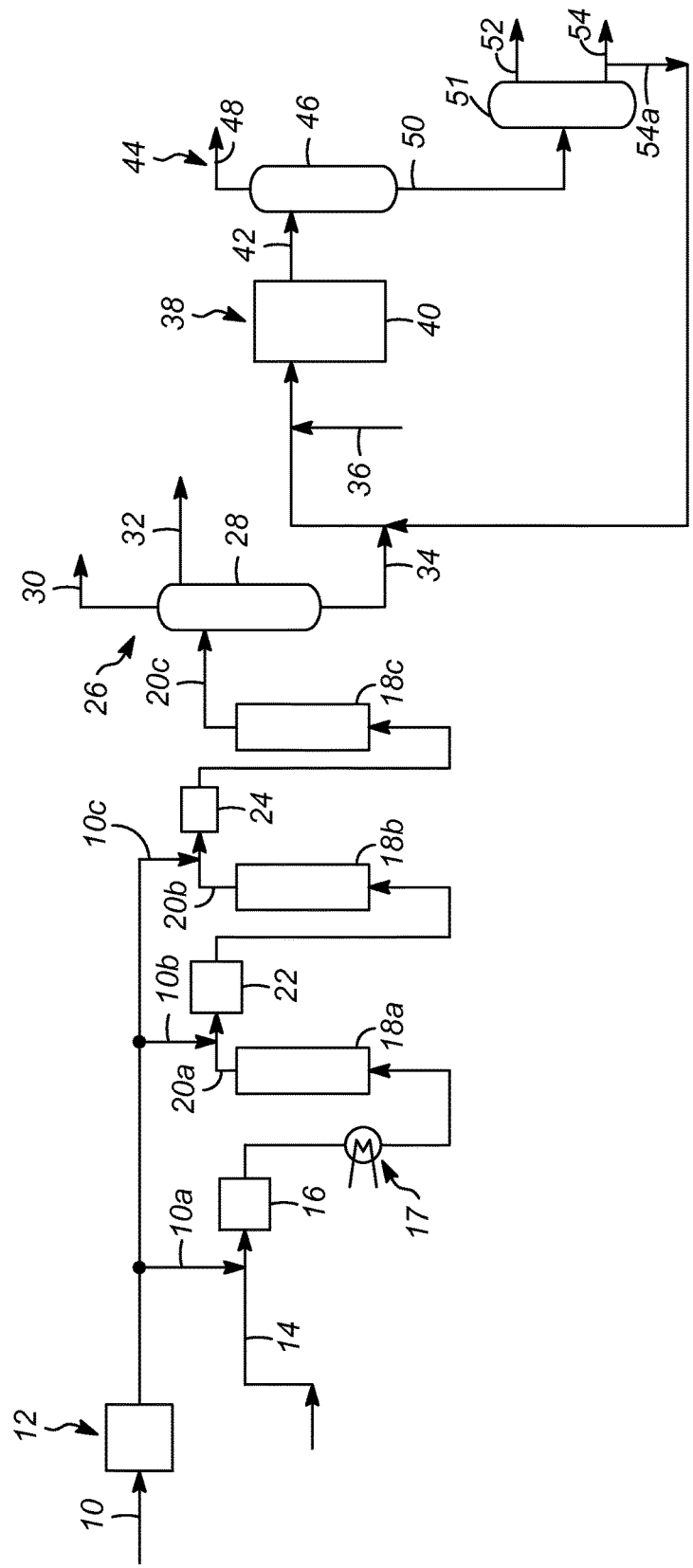

PROCESS FOR THE PRODUCTION OF JET-RANGE HYDROCARBONS BY OLIGOMERIZATION OF RENEWABLE OLEFINS HAVING 3 TO 8 CARBONS

FIELD OF THE INVENTION

The present disclosure generally relates to methods for producing renewable fuels and chemicals from biorenewable sources and the renewable fuels and chemicals produced thereby, and more particularly relates to methods for producing jet-range hydrocarbons from alkanols, including for example isobutanol.

BACKGROUND OF THE INVENTION

As the worldwide demand for fuel increases, interest in sources other than crude oil from which to produce transportation fuels, including aviation fuels, is ever increasing. For example, due to the growing environmental concerns over fossil fuel extraction and economic concerns over exhausting fossil fuel deposits, there is a demand for using an alternate or "green" feed source for producing hydrocarbons for use as transportation fuels and for use in other industries. Such sources of interest include, for example, biorenewable sources, such as vegetable and seed oils, animal fats, and algae byproducts, among others as are well-known to those skilled in the art. A conventional catalytic hydro-processing technique is known for converting a biorenewable feedstock into green diesel fuel that may be used as a substitute for the diesel fuel produced from crude oil. As used herein, the terms "green diesel fuel" and "green jet fuel" refer to fuel produced from biorenewable sources, in contrast to those produced from crude oil. The process also supports the possible co-production of propane and other light hydrocarbons, as well as naphtha or green jet fuel.

Biomass fermentation products typically include lower isoalkanols such as, for example, $C_3$ to $C_8$ isoalkanols obtained by contacting biomass with biocatalysts that facilitate conversion (by fermentation) of the biomass to isoalkanols of interest. The biomass feedstock for such fermentation processes can be any suitable fermentable feedstock known in the art, such as fermentable sugars derived from agricultural crops including sugarcane, corn, etc. Suitable fermentable biomass feedstock can also be prepared by the hydrolysis of biomass, for example lignocellulosic biomass (e.g. wood, corn stover, switchgrass, herbiage plants, ocean biomass, etc.), to form fermentable sugars.

Jet-range fuels are an important product for the aerospace industry and the military. The specific characteristics of various grades and types of jet-range fuels vary slightly according to the particular application and environment in which they are used. Generally, jet-range fuels comprise a mixture of primarily $C_8$ to $C_{16}$ hydrocarbons and typically have a freezing point of about −40 or −47° C. (−40 or −52.6° F.). In order to produce jet-range fuels from isoalkanols derived from fermented biomass, in one example known in the art, isobutanol is first dehydrated to form butenes. The butenes are then oligomerized, in the presence of an oligomerization catalyst, in one or more reactors to form heavier olefins, such as $C_5$ to $C_{20}$, or even higher, olefinic oligomers. Finally, the resulting olefinic oligomers are hydrogenated in a saturation reactor to form the corresponding $C_5$ to $C_{20}$, or even higher, paraffins in a mixture which can then be subjected to separation to obtain $C_9$ to $C_{20+}$ paraffins suitable for use as biorenewable jet fuel.

Since the oligomerization reaction is highly exothermic, the butene fed to the oligomerization reactors may be cooled before entering the oligomerization reactors. Another measure taken to control the temperature increase in the oligomerization reactors is to limit the proportion of olefins contained in the feedstream provided to each reactor to no more than about 15 percent by weight (wt %). This is accomplished, at least in part, by adding non-reactive diluent material to the reactors which also provides a heat sink to control the temperature rise in the reactors.

Typically, this dilution may be done by recycling saturated distillate product from a stripped effluent of a hydrogenation section back to the oligomerization and hydrogenation reactors. The saturated recycle is, for the most part, inert across the hydrogenation reactor. Nevertheless, while the diluent does control the temperature, it may impose limitations on the processing.

Therefore, it would be desirable to have one or more processes which efficiently and effectively dilute a feedstock to an oligomerization reactor.

SUMMARY OF THE INVENTION

One or more processes have been invented in which a renewable olefin feedstock comprising $C_3$ to $C_8$ olefins to an oligomerization reaction zone is split into two or more streams with each stream being passed to a separate reactor and in which an effluent from an upstream reactor is used to dilute the stream of renewable olefin feedstock to a downstream reactor.

Accordingly, in a first aspect of the invention, the present invention may be broadly characterized as providing a process for producing jet range hydrocarbons by: splitting a renewable olefin feedstock comprising $C_3$ to $C_8$ olefins into at least a first olefin feedstock and a second olefin feedstock; oligomerizing the first olefin feedstock in a first oligomerization reactor containing a catalyst and being operated under conditions to produce a first oligomerized effluent; oligomerizing the second olefin feedstock in a second oligomerization reactor containing a catalyst and being operated under conditions to produce a second oligomerized effluent; and separating jet range olefins from the second oligomerized effluent. The second oligomerized effluent includes at least a portion of the first oligomerized effluent, and both the first olefin feedstock and the second olefin feedstock are diluted prior to oligomerization.

In one or more embodiments of the present invention, the process includes diluting the first olefin feedstock with a saturated hydrocarbon.

In some embodiments of the present invention, the process includes: diluting the second olefin feedstock with the first oligomerized effluent.

In various embodiments of the present invention, the first olefin feedstock and the second olefin feedstock comprise different amounts.

In at least one embodiment of the present invention, the process includes hydrogenating the distillate range olefins to provide a jet range fuel.

In one or more embodiments of the present invention, the process includes splitting the renewable olefin feedstock into at least the first olefin feedstock, the second olefin feedstock, and a third olefin feedstock and, oligomerizing the third olefin feedstock in a third oligomerization reactor containing a catalyst and being operated under conditions to produce a third oligomerized effluent. The third olefin feedstock is diluted prior to oligomerization, and the third oligomerized effluent includes at least a portion of the first oligomerized effluent and the second oligomerized effluent. It is contemplated that the process also includes diluting the third olefin feedstock with the second oligomerized effluent. It is also contemplated that the process includes diluting the second olefin feedstock with the first oligomerized effluent. It is further contemplated that the first olefin feedstock, the second olefin feedstock, and the third olefin feedstock comprise different amounts.

In a second aspect of the present invention, the present invention may be broadly characterized as providing a process for producing jet range hydrocarbons by: splitting a renewable olefin feedstock into at least a first olefin feedstock and a second olefin feedstock; diluting the first olefin feedstock to provide a diluted first olefin feedstock; passing the diluted first olefin feedstock to a first oligomerization reactor containing a catalyst and being operated under conditions to produce a first oligomerized effluent; diluting the second olefin feedstock with the first oligomerized effluent to provide a diluted second olefin feedstock; passing the diluted second olefin feedstock to a second oligomerization reactor containing a catalyst and being operated under conditions to produce a second oligomerized effluent; and, hydrogenating at least a portion of the second oligomerized effluent in a hydrogenation zone to provide a jet range fuel stream.

In one or more embodiments of the present invention, the first olefin feedstock and the second olefin feedstock comprise different amounts.

In at least one embodiment of the present invention, the first olefin feedstock and the second olefin feedstock comprise the same amount.

In various embodiments of the present invention, the process includes splitting a third olefin feedstock from the renewable olefin feedstock, diluting the third olefin feedstock to provide a diluted third olefin feedstock, and, passing the diluted third olefin feedstock to a third oligomerization reactor containing a catalyst and being operated under conditions to produce a third oligomerized effluent. It is contemplated that the process includes passing the third oligomerized effluent to a separation zone configured to separate the third oligomerized effluent into at least a distillate range olefin stream, and, passing the distillate range olefin stream to the hydrogenation zone. It is also contemplated that the first olefin feedstock, the second olefin feedstock, and the third olefin feedstock comprise different amounts. It is further contemplated that the third olefin feedstock is greater than the second olefin feedstock. It is also contemplated that the second olefin feedstock is greater than the first olefin feedstock.

In some embodiments of the present invention, the renewable olefin feedstock comprises substantially $C_4$ olefins.

In at least one embodiment of the present invention, the process includes cooling a diluted olefin feedstock in a cooling zone prior to passing the diluted olefin feedstock to an oligomerization reactor.

In one or more embodiments of the present invention, the process includes splitting the renewable olefin feedstock into a plurality of olefin feedstocks, passing each renewable olefin feedstock to an oligomerization reactor, and, diluting at least some of the olefin feedstocks with an effluent stream from an oligomerization reactor.

Additional aspects, embodiments, and details of the invention, which may be combined in any manner, are set forth in the following detailed description of the invention.

DETAILED DESCRIPTION OF THE DRAWINGS

One or more exemplary embodiments of the present invention will be described below in conjunction with the following drawing FIGURE, in which:

the FIGURE shows a process flow diagram of one or more processes according to the present invention.

DETAILED DESCRIPTION OF THE INVENTION

As used herein, the term "stream" can include various hydrocarbon molecules and other substances. Moreover, the term "stream comprising $C_x$ hydrocarbons" or "stream comprising $C_x$ olefins" can include a stream comprising hydrocarbon or olefin molecules, respectively, with "x" number of carbon atoms, suitably a stream with a majority of hydrocarbons or olefins, respectively, with "x" number of carbon atoms and preferably a stream with at least 75 wt % hydrocarbons or olefin molecules, respectively, with "x" number of carbon atoms. Moreover, the term "stream comprising $C_x$+ hydrocarbons" or "stream comprising $C_x$+ olefins" can include a stream comprising a majority of hydrocarbon or olefin molecules, respectively, with more than or equal to "x" carbon atoms and suitably less than 10 wt % and preferably less than 1 wt % hydrocarbon or olefin molecules, respectively, with x−1 carbon atoms. Lastly, the term "$C_x$− stream" can include a stream comprising a majority of hydrocarbon or olefin molecules, respectively, with less than or equal to "x" carbon atoms and suitably less than 10 wt % and preferably less than 1 wt % hydrocarbon or olefin molecules, respectively, with x+1 carbon atoms.

As used herein, the term "zone" can refer to an area including one or more equipment items and/or one or more sub-zones. Equipment items can include one or more reactors or reactor vessels, heaters, exchangers, pipes, pumps, compressors, controllers and columns. Additionally, an equipment item, such as a reactor, dryer, or vessel, can further include one or more zones or sub-zones.

As used herein, the term "substantially" can mean an amount of at least generally about 70%, preferably about 80%, and optimally about 90%, by weight, of a compound or class of compounds in a stream.

As used herein, the term "gasoline" can include hydrocarbons having a boiling point temperature in the range of about 25 to about 200° C. (68 to 392° F.) at atmospheric pressure.

As used herein the term "naphtha" can mean $C_5$ hydrocarbons up to hydrocarbons having a boiling point of 150° C. (302° F.) (i.e., hydrocarbons having a boiling point in the range of 30 to 150° C. (86 to 302° F.)).

As used herein the term "diesel" can include hydrocarbons having a boiling point temperature in the range of about 250 to about 400° C. (482 to 752° F.) at atmospheric pressure.

As used herein the term "jet-range hydrocarbons," "jet-range paraffins," "jet-range fuels," or "jet fuels" can include hydrocarbons having a boiling point temperature in the range of about 130 to about 300° C. (266 to 572° F.), preferably 150 to 260° C. (302 to 500° F.), at atmospheric pressure. Additionally, as used herein, the terms "jet-range hydrocarbons," "jet-range paraffins," "jet-range fuels," or "jet fuels" refer to a mixture of primarily $C_8$ to $C_{16}$ hydrocarbons with a freezing point of about −40° C. (−40° F.) or about −47° C. (−52.6° F.).

As used herein, the term "distillate" comprises a mixture of diesel and jet-range hydrocarbons and can include hydrocarbons having a boiling point temperature in the range of about 150 to about 400° C. (302 to 752° F.) at atmospheric pressure.

As used herein, the phrase "a mixture of primarily . . . " or "comprising primarily . . . " a specified range of carbonnumbered hydrocarbons means that the group or category of hydrocarbons being described may also contain very small amounts of hydrocarbons outside the stated carbon number range, without altering the general characteristics (e.g., boiling point) of the group or category being described. For example, the description that jet fuels are a mixture of primarily $C_8$ to $C_{16}$ hydrocarbons means that jet fuels contain at least 80 wt % of hydrocarbon molecules each having from about 8 to about 16 carbon atoms with, possibly, very small amounts of hydrocarbon molecules each having less than about 8 carbon atoms, as well as very small amounts of hydrocarbon molecules each having more than 16 carbon atoms, such that the freezing point remains about −40° C. to about −47° C. (−40 to 52.6° F.). There are multiple standards, established by various industries and governments, that are useful for ensuring that particular types of jet fuels have uniform characteristics that fall within expected ranges. For example, one type of jet fuel, known as Aviation Turbine Fuel, Jet A, or Jet A-1 fuel, is composition of hydrocarbons that boil in a range such that the volatility characteristics of the hydrocarbon (or paraffinic form of the hydrocarbon after hydrogenation) substantially conform to the volatility standards of flash point (typically minimum of 38° C. (100° F.), distillation range (T10 boiling point maximum of 205° C. (401° F.) and final boiling point (maximum of 300° C. (572° F.), with all distillation valves measured by D86 or D2887 values converted to D86) set forth in ASTM D7566-11a, "Standard Specification for Aviation Turbine Fuel Containing Synthesized Hydrocarbons," promulgated by ASTM International, Inc. of West Conshohoken, Pa. Other standards that provide parameters useful for characterizing and defining the jet fuels prepared using the methods and apparatus contemplated and described herein include Jet Propellant (JP)-5 and JP-8, which are set forth in the United States military specifications found at MIL-DTL-83133, as well as in British Defence Standard 91-87.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures."

As used herein, "taking a stream from" means that some or all of the original stream is taken.

As mentioned above, one or more methods have been invented for producing jet-range hydrocarbons from one or more biorenewable $C_3$ to $C_8$ olefins via oligomerization. The oligomerization reactor is highly exothermic and in order to control the temperature rise from the inlet to the outlet of the reactor (i.e., ΔT), various processes utilize a diluent. In order to increase the processing yield, the present invention proposes to split the feedstock into a plurality of streams, each being injected into a reactor, the reactors being arranged in series. The effluent from an upstream reactor will dilute the feedstock to a downstream reactor. While these methods find greatest utility in converting feedstocks from alkanols, thereby allowing for production of jet fuels from renewable sources, this is not intended to limit the application of the methods of the present invention.

With these general principles in mind, one or more embodiments of the present invention will be described with the understanding that the following description is not intended to be limiting.

As shown in the FIGURE, one or more processes of the present invention include a renewable olefin feedstock 10 being passed to an oligomerization zone having one or more oligomerization reactors 18a, 18b, 18c. While three oligomerization reactors 18a, 18b, 18c have been shown, it should be appreciated that any number may be used. As used herein, the term "renewable" denotes that the carbon content of the olefin feedstock 10 is from a "new carbon" source as measured by ASTM test method D6866-05, "Determining the Bio-based Content of Natural Range Materials Using Radiocarbon and Isotope Ratio Mass Spectrometry Analysis", incorporated herein by reference in its entirety. This test method measures the $^{14}C/^{12}C$ isotope ratio in a sample and compares it to the $^{14}C/^{12}C$ isotope ratio in a standard 100% bio-based material to give percent bio-based content of the sample. Additionally, "bio-based materials" are organic materials in which the carbon comes from recently (on the order of centuries) fixated carbon dioxide present in the atmosphere using sunlight energy (photosynthesis). On land, this carbon dioxide is captured or fixated by plant life (e.g., agricultural crops or forestry materials). In the oceans, the carbon dioxide is captured or fixated by photosynthesizing bacteria or phytoplankton. For example, a bio-based material has a $^{14}C/^{12}C$ isotope ratio greater than zero. Contrarily, a fossil-based material has a $^{14}C/^{12}C$ isotope ratio of zero. The term "renewable" with regard to compounds such as alcohols or hydrocarbons (olefins, di-olefins, polymers, etc.) also refers to compounds prepared from biomass using thermochemical methods (e.g., Fischer-Tropsch catalysts), biocatalysts (e.g., fermentation), or other processes, for example as described herein.

A small amount of the carbon atoms in the carbon dioxide in the atmosphere is the radioactive isotope $^{14}C$. This $^{14}C$ carbon dioxide is created when atmospheric nitrogen is struck by a cosmic ray generated neutron, causing the nitrogen to lose a proton and form carbon of atomic mass 14 ($^{14}C$), which is then immediately oxidized, to carbon dioxide. A small but measurable fraction of atmospheric carbon is present in the form of $^{14}C$.

Atmospheric carbon dioxide is processed by green plants to make organic molecules during the process known as photosynthesis. Virtually all forms of life on Earth depend on this green plant production of organic molecules to produce the chemical energy that facilitates growth and reproduction. Therefore, the $^{14}C$ that forms in the atmosphere eventually becomes part of all life forms and their biological products, enriching biomass and organisms which feed on biomass with $^{14}C$. In contrast, carbon from fossil fuels does not have the signature $^{14}C/^{12}C$ ratio of renewable organic molecules derived from atmospheric carbon dioxide. Furthermore, renewable organic molecules that biodegrade to carbon dioxide do not contribute to an increase in atmospheric greenhouse gases as there is no net increase of carbon emitted to the atmosphere. Assessment of the renewably based carbon content of a material can be performed through standard test methods, e.g., using radiocarbon and isotope ratio mass spectrometry analysis. ASTM International (formally known as the American Society for Testing and Materials) has established a standard method for assessing the bio-based content of materials. The ASTM method is designated ASTM-D6866. The application of ASTM-D6866 to derive "bio-based materials" is built on the same concepts as radiocarbon dating, but without use of the age equations. The analysis is performed by deriving a ratio of the amount of radiocarbon ($^{14}C$) in an unknown sample compared to that of a modern reference standard. This ratio is reported as a percentage with the units "pMC" (percent modern carbon). If the material being analyzed is a mixture of present day radiocarbon and fossil carbon (containing very low levels of radiocarbon), then the pMC value obtained correlates directly to the amount of biomass material present in the sample.

Returning to the FIGURE, the renewable olefin feedstock 10 includes at least $C_4$ olefins, preferably comprising $C_3$ to $C_8$ olefins. In an aspect, the renewable olefin stream may comprise one or more carbon number olefins such as $C_3$ to $C_4$ olefins or $C_3$ to $C_5$ olefins or $C_4$ to $C_5$ olefins or $C_3$ to $C_6$ olefins. The renewable olefins may be derived from their corresponding alcohols (i.e., $C_4$ alcohols, especially including isobutanol), which are typically formed by fermentation or by condensation reactions of synthesis gas. For example, a feedstock for the fermentation process can be any suitable fermentable feedstock known in the art, such as sugars derived from agricultural crops including sugarcane, corn, etc. Alternatively, the fermentable feedstock can be prepared by the hydrolysis of biomass, for example lignocellulosic biomass (e.g. wood, corn stover, switchgrass, herbiage plants, ocean biomass, etc.). In another example, renewable alcohols, such as isobutanols, can be prepared photosynthetically, for example using cyanobacteria or algae engineered to produce isobutanol and/or other alcohols. When produced photosynthetically, the feedstock for producing the resulting renewable alcohols is light, water, and carbon dioxide, which is provided to the photosynthetic organism (e.g., cyanobacteria or algae). Additionally, other known methods, whether biorenewable or otherwise, for producing isobutanol are suitable for supplying the $C_4$ olefins; the methods described herein are not intended to be limited by the use of any particular renewable feed source. Typically, the renewable olefin feedstock 10 may comprise greater than 50 wt % olefins such as greater than 70 wt % or greater than 80 wt % or greater than 90 wt % olefins or greater than 95 wt % or greater than 99 wt % olefins.

Olefin isomer types of the renewable olefin feedstock 10, and of the oligomers produced by oligomerization, can be denominated according to the degree of substitution of the double bond, as follows:

TABLE 1

| Olefin Type | Structure | Description |
| --- | --- | --- |
| I | R—HC=$CH_2$ | Monosubstituted |
| II | R—HC=CH—R | Disubstituted |
| III | $RRC=CH_2$ | Disubstituted |
| IV | RRC=CHR | Trisubstituted |
| V | RRC=CRR | Tetrasubstituted | wherein R represents an alkyl group, each R being the same or different. Type I compounds are sometimes described as α- or vinyl olefins and Type III as vinylidene olefins. Type IV is sometimes subdivided to provide a Type IVA, in which access to the double bond is less hindered, and Type IVB where it is more hindered. In an aspect, the renewable olefin feedstock 10 may comprise high quantities of Type I olefins such as greater than 50 wt % or greater than 70 wt % or greater than 85 wt % or greater than 90 wt % or greater than 95 wt % Type I olefins as a fraction of the total olefins in the renewable olefins stream.

The renewable olefins (possibly derived and converted from the $C_4$ alcohols, for example by dehydration of the alcohol, see, e.g., U.S. Pat. No. 4,423,251) in the renewable olefin feedstock 10 may be passed first to an oxygenate removal zone 12 to remove water and any remaining oxygenates. The oxygenate removal zone 12 may comprise a water wash, one or more driers, or other similar processing equipment capable of removing water and oxygenates.

In the various embodiments of the present invention, the renewable feedstock 10 is split into a plurality of streams of olefin feedstock 10a, 10b, 10c. While the depicted embodiment shows three streams 10a, 10b, 10c, two streams or more than three streams may be used.

The first olefin feedstock stream 10a is mixed with a diluent stream 14 to form a diluted stream which is passed to a feed cooler 16. The diluent stream 14 may comprise saturated hydrocarbons, or in some embodiments, olefins, especially heavy olefins.

From the feed cooler 16, the first olefin feedstock stream 10a (including the diluent stream 14) may be heated in a heat exchange zone and then passed to a first oligomerization reactor 18a. In the first oligomerization reactor 18a, at least a portion of the renewable olefins are converted into a mixture of heavier boiling hydrocarbons including jet range hydrocarbons via oligomerization by reacting the olefins using a zeolitic oligomerization catalyst under appropriate conditions to provide a first oligomerized effluent 20a. For example, the first oligomerization reactor 18a, for example, without limitation, may be operated at a temperature from about 100 to about 300° C. (212 to 572° F.) and a pressure of from about 689 to about 6895 kPa (100 to 1000 psig). For example, the operating temperature may be from about 120 to about 280° C. (248 to 536° F.), or even from about 160 to about 260° C. (320 to 402.8° F.). The operating pressure may, for example, be from about 1034 to about 5516 kPa (150 to 800 psi), or even from about 2068 to about 4964 kPa (300 to 720 psi).

The oligomerization catalyst in the oligomerization zone is not limited to any particular catalyst and may comprise any catalyst suitable for catalyzing conversion of the one or more biorenewable $C_3$ to $C_8$ olefins in the olefin stream to olefinic oligomers comprising heavier boiling $C_{5+}$ hydrocarbons, including jet-range hydrocarbons. The oligomerization catalyst may be any such catalyst known now or in the future.

Conventional oligomerization catalysts will generally convert an olefin to a mixture of dimers, trimers, tetramers, and sometimes pentamers, of the olefin. For example, where the $C_3$ to $C_8$ olefin is isobutylene, a $C_4$ olefin, the products of oligomerization in the presence of a conventional oligomerization catalyst include $C_8$, $C_{12}$, $C_{16}$, and sometimes $C_{20}$ olefins, together in a mixture. Conventional oligomerization catalysts include, without limitation, solid phosphoric acid ("SPA") and certain ion exchange resins such as Amberlyst-36 (commercially available from The Dow Chemical Company of Midland, Mich., U.S.A.). The olefinic oligomer mixture produced using conventional oligomerization catalysts may be further subjected to a separation process to produce a mixture of jet-range hydrocarbons suitable for use as jet fuels. These jet fuels often have a boiling point distribution that has well-defined boiling point steps corresponding to only a few isomers of the corresponding trimer, tetramer, and pentamer paraffins of the starting olefin, which is different from petroleum-derived jet fuels.

Alternative oligomerization catalysts comprising zeolite materials, on the other hand, catalyze oligomerization conversion of $C_3$ to $C_8$ olefins to dimers, trimers, tetramers, and sometimes pentamers of the $C_3$ to $C_8$ olefins, but also catalyze backcracking conversion of the resulting heavier olefinic oligomers back into lighter and more random and varied sizes of olefins including $C_5$ to $C_{20+}$ hydrocarbons. In other words, under appropriate conditions, zeolitic catalysts such as, without limitation, MTT, TON, MFI, and MTW, yield $C_{5+}$ hydrocarbons, including jet-range hydrocarbons, with an increased distribution and variety of carbon numbers than those made using conventional non-zeolitic catalysts. This means that jet-range fuel produced from biorenewable olefins via oligomerization in the presence of zeolite catalysts has a boiling range and compositional profile that is more similar to jet-range fuels produced from petroleum refining processes.

Suitable zeolite catalysts may comprise between 5 and 95 wt % of zeolite material. Suitable zeolite materials include zeolites having a structure from one of the following classes: MFI, MEL, ITH, IMF, TUN, FER, BEA, FAU, BPH, MEI, MSE, MWW, UZM-8, MOR, OFF, MTW, TON, MTT, AFO, ATO, and AEL. 3-letter codes indicating a zeotype are as defined by the Structure Commission of the International Zeolite Association and are maintained at http://www.iza-structure.org/databases/. UZM-8 is as described in U.S. Pat. No. 6,756,030. In a preferred aspect, the zeolite catalyst may comprise a zeolite with a framework having a ten-ring pore structure. Examples of suitable zeolites having a ten-ring pore structure include TON, MTT, MFI, MEL, AFO, AEL, EUO and FER. The oligomerization catalyst comprising a zeolite having a ten-ring pore structure may comprise a uni-dimensional pore structure. A uni-dimensional pore structure indicates zeolite materials containing non-intersecting pores that are substantially parallel to one of the axes of the crystal. The pores preferably extend through the zeolite crystal. Suitable examples of zeolite materials having a ten-ring uni-dimensional pore structure may include MTT. In a further aspect, the oligomerization catalyst comprises an MTT zeolite.

The zeolite catalyst may be formed by combining the zeolite material with a binder, and then forming the catalyst into pellets. The pellets may optionally be treated with a phosphorus reagent to create a zeolite having a phosphorous component between 0.5 and 15 wt % of the treated catalyst. The binder is used to confer hardness and strength on the catalyst. Binders include alumina, aluminum phosphate, silica, silica-alumina, zirconia, titania and combinations of these metal oxides, and other refractory oxides, and clays such as montmorillonite, kaolin, palygorskite, smectite and attapulgite. A preferred binder is an aluminum-based binder, such as alumina, aluminum phosphate, silica-alumina and clays.

One of the components of the zeolite catalyst binder utilized herein is alumina. The alumina source may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A suitable alumina is available from UOP LLC under the trademark Versal. A preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina.

A suitable zeolite catalyst may be, for example, prepared by mixing proportionate volumes of zeolite and alumina to achieve the desired zeolite-to-alumina ratio. In an embodiment, the MTT content may be about 5 to 85 wt %, for example about 20 to 82 wt % MTT zeolite, and the balance alumina powder will provide a suitably supported catalyst. A silica support is also contemplated.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried. Extrusion aids such as cellulose ether powders can also be added. A preferred extrusion aid is available from The Dow Chemical Company under the trademark Methocel.

The paste or dough may be prepared in the form of shaped particulates, with the preferred method being to extrude the dough through a die having openings therein of desired size and shape, after which the extruded matter is broken into extrudates of desired length and dried. A further step of calcination may be employed to give added strength to the extrudate. Generally, calcination is conducted in a stream of air at a temperature from about 260 to about 815° C. (500 to 1500° F.). The MTT catalyst is not selectivated to neutralize acid sites such as with an amine.

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 µm; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

Returning to the FIGURE, downstream from the first oligomerization reactor 18a, the second olefin feedstock stream 10b is diluted with the first oligomerized effluent 20a, to form a diluted stream, which is passed to a feed cooler 22. The second olefin feedstock stream 10b (diluted with the first oligomerized effluent 20a) is then passed to a second oligomerization reactor 18b which provides a second oligomerized effluent 20b—which will also include a portion of the first oligomerized effluent 20a. The second oligomerization reactor 18b may be operated in the same manner as the first oligomerization reactor 18a described above.

Downstream of the second oligomerization reactor 18b, the third olefin feedstock stream 10c is diluted with second first oligomerized effluent 20b (which will also include the first oligomerized effluent 20a) to form a combined stream which is passed to a feed cooler 24. The third olefin feedstock stream 10c (diluted with the second oligomerized effluent 20b) is then passed to a third oligomerization reactor 18c which provides a third oligomerized effluent 20c—which will include the second oligomerized effluent 20b and the first oligomerized effluent 20a. The third oligomerization reactor 18c may be operated in the same manner as the first oligomerization reactor 18a described above. Again, two or more oligomerization reactors may be used in accordance with the present invention and the depicted embodiment of three reactors is not intended to be limiting.

The amounts of the various streams of renewable olefin feedstock 10a, 10b, 10c, may be the same, but they are preferably different. In a most preferred embodiment, the amount of each stream of renewable olefin feedstock increases for the downstream reactors. In other words, based upon the depicted embodiment, the second olefin feedstock stream 10b, would be greater than the first olefin feedstock stream 10a. Similarly, the third olefin feedstock stream 10c, would be greater than the second olefin feedstock stream 10b (and also the first olefin feedstock stream 10a). Again, this is merely a preferred configuration and is not intended to be limiting.

Returning to the FIGURE, the third oligomerized effluent 20c, which comprises a net oligomerized effluent, may be passed to a separation zone 26 which may include at least one fractionation or distillation column 28. In the separation zone 26, the third oligomerized effluent 20c may be separated into, in at least one embodiment, a light hydrocarbon stream 30 comprising $C_{4-}$ hydrocarbons, a naphtha hydrocarbon stream 32 comprising $C_5$ to $C_7$ hydrocarbons, and a heavy stream 34 comprising $C_{8+}$ distillate range olefins. As will be appreciated, there may be some overlap between the components of the various streams. For example, the naphtha hydrocarbon stream 32 may include some $C_4$ hydrocarbons or some heavier hydrocarbons such as $C_8$ or $C_9$ hydrocarbons. It is preferred that such streams include at least 50% of the intended components (i.e., the naphtha hydrocarbon stream 32 comprises at least 50% $C_5$ to $C_7$ hydrocarbons).

The further processing of the light hydrocarbon stream 30 and the naphtha hydrocarbon stream 32 are not necessary for an understanding or practicing of the present invention.

Returning to the FIGURE, the heavy stream 34, along with a hydrogen containing gas 36 may be passed to a hydrogenation zone 38 having a hydrogenating reactor 40. In the hydrogenating reactor 40, hydrogenation may be performed using a conventional hydrogenation or hydrotreating catalyst, which may include metallic catalysts containing, e.g., palladium, rhodium, nickel, ruthenium, platinum, rhenium, cobalt, molybdenum, or combinations thereof, and the supported versions thereof. Catalyst supports can be any solid, inert substance including, but not limited to, oxides such as silica, alumina, titania, calcium carbonate, barium sulfate, and carbons. The catalyst support can be in the form of powder, granules, pellets, or the like. Hydrogenation suitably occurs at a temperature of about 150° C. (300° F.) and at a pressure of about 6895 kPa (1000 psig). Other process conditions known by those of ordinary skill in the art may be utilized.

A hydrogenated effluent 42 from the hydrogenation zone 38 will comprise mostly saturated distillate range hydrocarbons (i.e., paraffins). The hydrogenated effluent 42 may be passed to a second separation zone 44 to separate one or more product streams from the hydrogenated effluent 42. In an exemplary embodiment of the present invention, the second separation zone 44 may include a separator vessel or multiple separator vessels, such as a cold separator and/or hot separator vessel (not shown in FIGURE for simplicity), and/or one or more columns 46, 51 or other vessels configured to separate the saturated hydrocarbons.

In a preferred embodiment shown in the FIGURE, a first separation column 46 in the second separation zone 44 separates the hydrogenated effluent 42 into a vent gas stream 48 and a saturated distillate range stream 50. The further processing of the vent gas stream 48 is not important for the practicing of the present invention. As shown in the FIGURE, the saturated distillate range stream 50 may be passed to a second separation column 51 to separate the saturated distillate range stream 50 into a saturated jet range stream 52 and a saturated diesel range stream 54. The saturated jet range stream 52 comprises the desired jet-range hydrocarbons to be used as fuel or fuel blending component. Furthermore, a portion of the distillate range stream 50 may be used as a recycle stream to the hydrogenation zone 38 to be combined with the heavy stream 34 and hydrogen stream 36 to form a combined stream passed to the hydrogenating reactor 40. As shown in the FIGURE, a portion 54a of the saturated diesel range stream 54 is recycled back to the hydrogenating reactor 40. Although not shown, a portion of the saturated jet range stream 52 or a portion of the saturated distillate range stream 50 may be recycled back to the hydrogenating reactor 40.

In sum, by splitting the renewable feedstock into a plurality of streams and injecting each stream into a different reactor, the temperature in the various reactors can be controlled. The smaller reactors with less catalyst will have a lower cost and require less energy to operate and will provide comparable production yield. Furthermore, by using a series of reactors, the amount of a recycle stream may be minimized if desired.

It should be appreciated and understood by those of ordinary skill in the art that various other components such as valves, pumps, filters, coolers, separator vessels, etc. were not shown in the drawings as it is believed that the specifics of same are well within the knowledge of those of ordinary skill in the art and a description of same is not necessary for practicing or understating the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for producing distillate range hydrocarbons comprising:

splitting a renewable olefin feedstock comprising $C_3$ to $C_8$ olefins into at least a first olefin feedstock stream and a second olefin feedstock stream wherein the first olefin feedstock stream and the second olefin feedstock stream comprise different mass flow amounts;

diluting the first olefin feedstock stream to provide a diluted first olefin feedstock stream;

oligomerizing the diluted first olefin feedstock stream in a first oligomerization reactor containing a first non-selectivated MTT zeolite catalyst extrudate and being operated under conditions comprising a temperature of from 160 to 260° C. to produce a first oligomerized effluent;

diluting the second olefin feedstock stream with the first oligomerized effluent to provide a diluted second olefin feedstock stream;

oligomerizing the diluted second olefin feedstock stream in a second oligomerization reactor containing a second non-selectivated MTT zeolite catalyst extrudate and being operated under conditions comprising a temperature of from 160 to 260° C. to produce a second oligomerized effluent; and separating distillate range olefins from the second oligomerized effluent.

2. The process of claim 1 further comprising:
diluting the first olefin feedstock stream with a saturated hydrocarbon to provide the diluted first olefin feedstock stream.

3. The process of claim 1 further comprising:
hydrogenating a fraction of the distillate range olefins comprising $C_8+$ olefins to provide a distillate range stream.

4. The process of claim 1 further comprising:
splitting the renewable olefin feedstock into at least the first olefin feedstock stream, the second olefin feedstock stream, and a third olefin feedstock stream wherein the first olefin feedstock stream, the second olefin feedstock stream, and the third olefin feedstock stream comprise different mass flow amounts;
diluting the third olefin feedstock stream with the second oligomerized effluent to provide a diluted third olefin feedstock stream; and
oligomerizing the diluted third olefin feedstock stream in a third oligomerization reactor containing a third non-selectivated MTT zeolite catalyst extrudate and being operated under conditions comprising a temperature of from 160 to 260° C. to produce a third oligomerized effluent.

5. A process for producing distillate range hydrocarbons comprising:
splitting a renewable olefin feedstock comprising $C_3$ to $C_8$ olefins into at least a first olefin feedstock stream and a second olefin feedstock stream wherein the first olefin feedstock stream and the second olefin feedstock stream comprise different mass flow amounts;
diluting the first olefin feedstock stream to provide a diluted first olefin feedstock stream;
passing the diluted first olefin feedstock stream to a first oligomerization reactor containing a non-selectivated MTT zeolite catalyst extrudate and being operated under conditions comprising a temperature of from 160 to 260° C. to produce a first oligomerized effluent;
diluting the second olefin feedstock stream with the first oligomerized effluent to provide a diluted second olefin feedstock stream;
passing the diluted second olefin feedstock stream to a second oligomerization reactor containing the non-selectivated MTT zeolite catalyst extrudate and being operated under conditions comprising a temperature of from 160 to 260° C. to produce a second oligomerized effluent; and
hydrogenating at least a portion of the second oligomerized effluent in a hydrogenation zone to provide a jet range fuel stream.

6. The process of claim 5 further comprising:
splitting a third olefin feedstock stream from the renewable olefin feedstock wherein the first olefin feedstock stream, the second olefin feedstock stream, and the third olefin feedstock stream comprise different amounts;
diluting the third olefin feedstock stream; and
passing the diluted third olefin feedstock stream to a third oligomerization reactor containing a third non-selectivated MTT zeolite catalyst and being operated under conditions comprising a temperature of from 160 to 260° C. to produce a third oligomerized effluent.

7. The process of claim 6 further comprising:
passing the third oligomerized effluent to a separation zone configured to separate the third oligomerized effluent into at least a distillate range olefin stream; and,
passing the distillate range olefin stream to the hydrogenation zone.

8. The process of claim 6 wherein the mass of the third olefin feedstock stream is greater than the mass of the second olefin feedstock stream.

9. The process of claim 8 wherein the mass of the second olefin feedstock stream is greater than the mass of the first olefin feedstock stream.

10. The process of claim 5 wherein the renewable olefin feedstock stream comprises substantially $C_4$ olefins.

11. The process of claim 5 further comprising:
cooling the renewable olefin feedstock stream, the first olefin feedstock stream, or the second olefin feedstock stream in a cooling zone.

* * * * *